US00PP12663P2

(12) United States Plant Patent
Heemskerk

(10) Patent No.: US PP12,663 P2
(45) Date of Patent: May 28, 2002

(54) HOSTA PLANT NAMED 'KARIN'

(75) Inventor: Gerard Heemskerk, Noordwijk (NL)

(73) Assignee: Future Plants V.O.F., Noordwijk (NL)

( * ) Notice: Subject to any disclaimer, the term of this patent is extended or adjusted under 35 U.S.C. 154(b) by 0 days.

(21) Appl. No.: 09/642,989

(22) Filed: Aug. 22, 2000

(51) Int. Cl.[7] ..... A01H 5/00
(52) U.S. Cl. ..... Plt./353
(58) Field of Search ..... Plt./353

(56) References Cited

U.S. PATENT DOCUMENTS

PP10,661 P * 10/1998 Heemskerk ..... Plt./353

OTHER PUBLICATIONS

UPOV–ROM GTITM Computer Database, GTI JOUVE Retrieval Software, citations for 'Karin' 2001/02.*

* cited by examiner

*Primary Examiner*—Bruce R. Campell
*Assistant Examiner*—Wendy A Baker
(74) *Attorney, Agent, or Firm*—C. A. Whealy

(57) ABSTRACT

A distinct cultivar of Hosta plant named 'Karin', characterized by its green and white variegated leaf color; thick leaves; relatively compact plant habit; and lavender-colored flowers that are positioned above the foliage on strong and erect scapes.

2 Drawing Sheets

BACKGROUND OF THE INVENTION

The present Invention relates to a new and distinct cultivar of Hosta plant, botanically known as *Hosta Fortunei,* and hereinafter referred to by the cultivar name Karin.

The new Hosta was discovered by the Inventor in a controlled environment in Noordwijk, The Netherlands, as a whole plant mutation of the *Hosta Fortunei* cultivar *Aureo-marginata,* not patented, in 1994. Plants of the new Hosta have a wider and more white margin than plants of the cultivar *Aureo-marginata.*

Asexual reproduction of the new cultivar by divisions harvested in Noordwijk, The Netherlands, has shown that the unique features of this new Hosta are stable and reproduced true to type in successive generations.

SUMMARY OF THE INVENTION

Plants of the cultivar Karin have not been observed under all possible environmental and cultural conditions. The phenotype may vary somewhat with variations in environment such as temperature, light intensity, daylength, irrigation amount and frequency, and/or fertilizer rate without, however, any variance in genotype.

The following traits have been repeatedly observed and are determined to be the unique characteristics of 'Karin'. These characteristics in combination distinguish 'Karin' as a new and distinct cultivar:

1 1. Dark green and white variegated leaf color.

1 2. Thick leaves.

1 3. Relatively compact growth habit.

1 4. Lavender-colored flowers that are positioned above the foliage on strong and erect scapes.

Plants of the new Hosta can be compared to plants of the variegated *Hosta Fortunei* cultivar Francee, not patented. Compared to plants of the new Hosta, plants of the cultivar Francee have a narrower leaf margin and thinner leaves.

BRIEF DESCRIPTION OF THE PHOTOGRAPHS

The accompanying colored photographs illustrate the overall appearance of the new Hosta, showing the colors as true as it is reasonably possible to obtain in colored reproductions of this type. Colors in the photographs may differ slightly from the color values cited in the detailed botanical description which more accurately describe the actual colors of the new Hosta.

The photograph on the first sheet comprises a side perspective view of a typical flowering plant of 'Karin' grown in a container.

The photograph at the top of the second sheet is a close-up view of typical flowers of 'Karin'.

The photograph at the bottom of the second sheet is a close-up view of the upper surface of a typical flower, a typical floral bract, and a typical leaf of 'Karin'.

DETAILED BOTANICAL DESCRIPTION

In the following description, color references are made to The Royal Horticultural Society Colour Chart except where general terms of ordinary dictionary significance are used. Plants used for the following description were about 40 weeks old and grown in containers under field conditions which closely approximate commercial production conditions during the spring and summer in Noordwijk, The Netherlands.

Botanical classification: *Hosta Fortunei* cultivar Karin.
Parentage: Whole plant mutation of *Hosta Fortunei* cultivar *Aureo-marginata,* not patented.
Propagation:
*Type cutting.*—By divisions.
*Rooting time.*—Divisons harvested in the spring develop roots in about 40 days at 15 to 20° C.
*Root description.*—Fleshy.

Plant description:

*Form.*—Perennial flowering plant; initially upright becoming outwardly arching as leaves develop; inverted triangle. Moderately clumping. Appropriate for 17-cm containers.

*Crop time.*—After rooting, about 40 weeks are required to produce finished flowering plants in 17-cm containers.

*Plant height.*—From soil level to top of leaf plane: About 30 cm. From soil level to top of flowering stems: About 55 cm.

*Plant diameter.*—About 50 cm.

*Vigor.*—Moderately vigorous.

*Foliage description.*—Leaves basal, simple, generally symmetrical, and long-persisting. Length: About 15 cm. Width: About 10.5 cm. Shape: Ovate to broadly ovate. Apex: Acute. Base: Rounded to cuneate. Margin: Entire. Texture: Glabrous, dull to slightly glossy. Petiole: Length: About 15 cm. Diameter: About 1 cm. Color: Young foliage, upper surface: Center, 137A; margins, 150B. Young foliage, lower surface: Center, 189B; margins, 150C. Mature foliage, upper surface: Center, 137A; margins, 150D, to white, close to 155C. Mature foliage, lower surface: Center, 189B; margins, 158A to 158B. Petiole color: Center, 137B to 138A; margins, 155C.

Flower description:

*Appearance.*—Single campanulate flowers with fused perianth arranged on one-sided racemes. Flowering stems arise from leaf axils. Typically two flowering stems per plant. Flowers not persistent.

*Quantity of flowers.*—About 20 flowers per raceme.

*Natural flowering season.*—Summer in the Netherlands; flowering continuous.

*Fragrance.*—Very faint and dull, pleasant.

*Flower longevity.*—About 4 to 7 days.

*Flower size.*—Length: About 7 cm. Diameter: About 3 cm.

*Flower buds* (*about 3 days before opening*).—Length: About 3.2 cm. Diameter: About 8 mm. Shape: Oblanceolate. Color: 76A to 86D.

*Perianth.*—Arrangement: Three interior and three exterior tepals; fused. Tepal length: About 6 cm. Tepal width: About 9 mm. Tepal shape: Elongated; apex, acute; margin, entire. Tepal texture: Smooth; glabrous. Tepal color: When opening, upper and lower surfaces: 76B to 76C. Fully opened, upper and lower surfaces: 76B to 76C; longitudinal stripes, 76A.

*Floral bracts.*—Arrangement: At pedicel base. Length: About 2.4 cm. Width: About 1.3 cm. Shape: Broadly lanceolate. Color: Green, close to 137B, with light lavender margin, 76C to 76D.

*Pedicel.*—Length: About 7 mm. Angle: Erect to about 50° from vertical; bent with weight of flower. Strength: Moderate to strong. Color: 85A.

*Scape.*—Length: About 55 cm. Aspect: Mostly upright. Texture: Smooth; glaucous. Color: 131A to 136A.

*Reproductive organs.*—Stamens: Quantity: Six; dorsifixed. Anther size: About 4 by 1.5 mm. Anther color: Dark purple. Pollen amount: Scarce. Pollen color: 15B. Pistils: Quantity: One. Pistil length: About 7 cm. Style length: About 6.8 cm. Style color: 150D; base, 145B. Stigma color: 157D. Ovary color: 145A.

*Seed description.*—Seed development has not been observed.

Disease resistance: Plants of the new Hosta have not been noted to be resistant to pathogens common to Hosta.

It is claimed:

1. A new and distinct cultivar of Hosta plant named 'Karin', as illustrated and described.

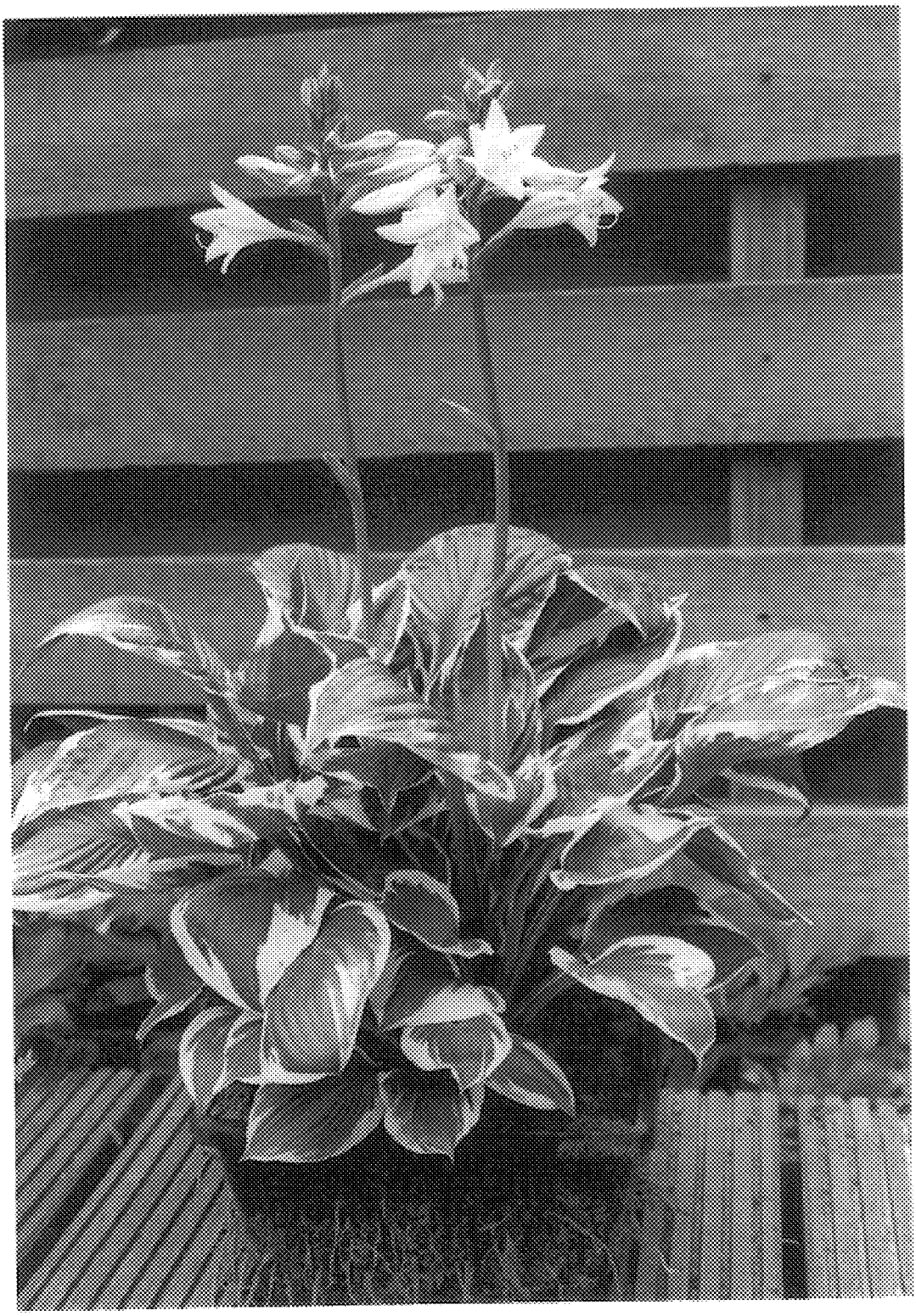

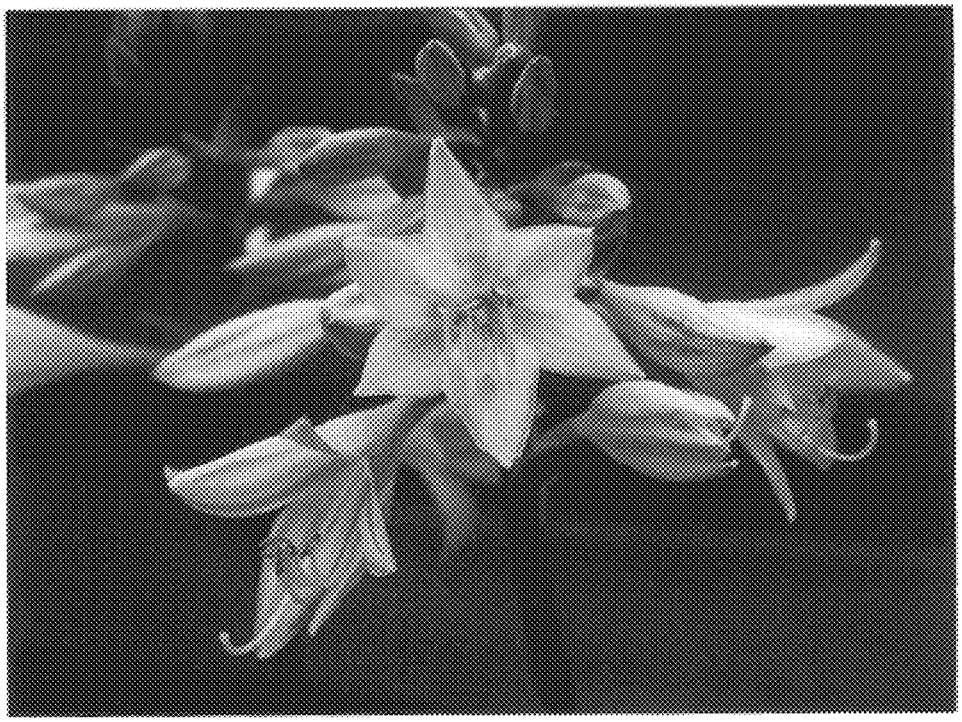
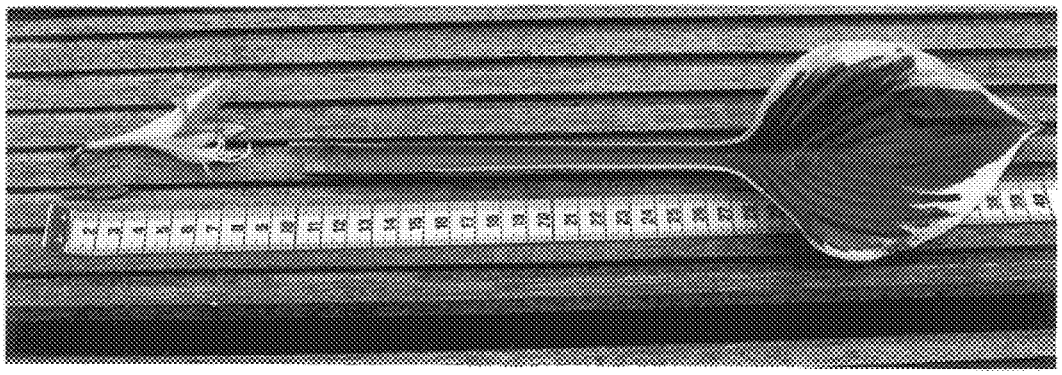

* * * * *